(12) United States Patent
Helmer et al.

(10) Patent No.: US 11,219,716 B2
(45) Date of Patent: Jan. 11, 2022

(54) SUPPLEMENTARY DEVICE FOR AN INJECTION DEVICE

(71) Applicant: Sanofi-Aventis Deutschland GMBH, Frankfurt am Main (DE)

(72) Inventors: Michael Helmer, Frankfurt am Main (DE); Ilario Melzi, Milan (IT); Bodin Hon, New Territories (HK)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 269 days.

(21) Appl. No.: 16/328,541

(22) PCT Filed: Aug. 29, 2017

(86) PCT No.: PCT/EP2017/071596
§ 371 (c)(1),
(2) Date: Feb. 26, 2019

(87) PCT Pub. No.: WO2018/041798
PCT Pub. Date: Mar. 8, 2018

(65) Prior Publication Data
US 2019/0201627 A1      Jul. 4, 2019

(30) Foreign Application Priority Data
Aug. 30, 2016   (EP) .................................... 16186288

(51) Int. Cl.
*A61M 5/31*      (2006.01)
*A61M 5/20*      (2006.01)
(Continued)

(52) U.S. Cl.
CPC .............. *A61M 5/31* (2013.01); *A61M 5/002* (2013.01); *A61M 5/2033* (2013.01);
(Continued)

(58) Field of Classification Search
CPC ................... A61M 5/31; A61M 5/002; A61M 2005/3126; A61M 2205/3306;
(Continued)

(56) References Cited

U.S. PATENT DOCUMENTS

| 10,661,001 B2 | 5/2020 | Thys |
| 2012/0211422 A1 | 8/2012 | Thys |

(Continued)

FOREIGN PATENT DOCUMENTS

| CN | 103402562 | 11/2013 |
| CN | 104797283 | 7/2015 |

(Continued)

OTHER PUBLICATIONS

International Preliminary Report on Patentability in Application No. PCT/EP2017/071596, dated Mar. 5, 2019, 8 pages.

(Continued)

*Primary Examiner* — Bradley J Osinski
(74) *Attorney, Agent, or Firm* — Fish & Richardson P.C.

(57) ABSTRACT

In one aspect the present disclosure refers to a supplementary device for an injection device, the supplementary device comprising: a body attachable to a housing of the injection device, the body having a first portion facing towards the housing when attached to the housing, at least one light source attached to the body, and at least a first optical coupling located in or at the first portion, connected to the at least one light source in a light transmissive way and optically connectable to a second optical coupling arranged in or on the housing.

14 Claims, 6 Drawing Sheets

(51) Int. Cl.
*A61M 5/00* (2006.01)
*A61M 5/50* (2006.01)

(52) U.S. Cl.
CPC ... *A61M 5/5086* (2013.01); *A61M 2005/3126* (2013.01); *A61M 2205/3306* (2013.01); *A61M 2205/3368* (2013.01); *A61M 2205/3375* (2013.01); *A61M 2205/3561* (2013.01); *A61M 2205/3569* (2013.01); *A61M 2205/52* (2013.01); *A61M 2205/583* (2013.01); *A61M 2205/587* (2013.01)

(58) Field of Classification Search
CPC ...... A61M 2205/3375; A61M 2205/52; A61M 2205/583; A61M 2205/587
See application file for complete search history.

(56) References Cited

U.S. PATENT DOCUMENTS

| | | | | |
|---|---|---|---|---|
| 2013/0226134 | A1* | 8/2013 | Schabbach | A61J 1/2093 604/500 |
| 2014/0163474 | A1* | 6/2014 | Draper | G05B 11/00 604/189 |
| 2015/0356273 | A1* | 12/2015 | Cave | G16H 30/20 705/2 |

FOREIGN PATENT DOCUMENTS

| | | |
|---|---|---|
| CN | 104918645 | 9/2015 |
| CN | 105142698 | 12/2015 |
| EP | 2206529 | 7/2010 |
| EP | 2823841 | 1/2015 |
| JP | 2014-507963 | 4/2014 |
| JP | 2016-508060 | 3/2016 |
| JP | 2016-520358 | 7/2016 |
| WO | WO 2009/024562 | 2/2009 |
| WO | WO 2012/080481 | 6/2012 |
| WO | WO 2014/053496 | 4/2014 |
| WO | WO 2014/111337 | 7/2014 |
| WO | WO 2014/173767 | 10/2014 |
| WO | WO 2014/173772 | 10/2014 |
| WO | WO 2015/136513 | 9/2015 |
| WO | WO 2015/165991 | 11/2015 |
| WO | WO 2015/167388 | 11/2015 |
| WO | WO 2016/118736 | 7/2016 |

OTHER PUBLICATIONS

International Search Report and Written Opinion in Application No. PCT/EP2017/071596, dated Nov. 15, 2017, 11 pages.

* cited by examiner

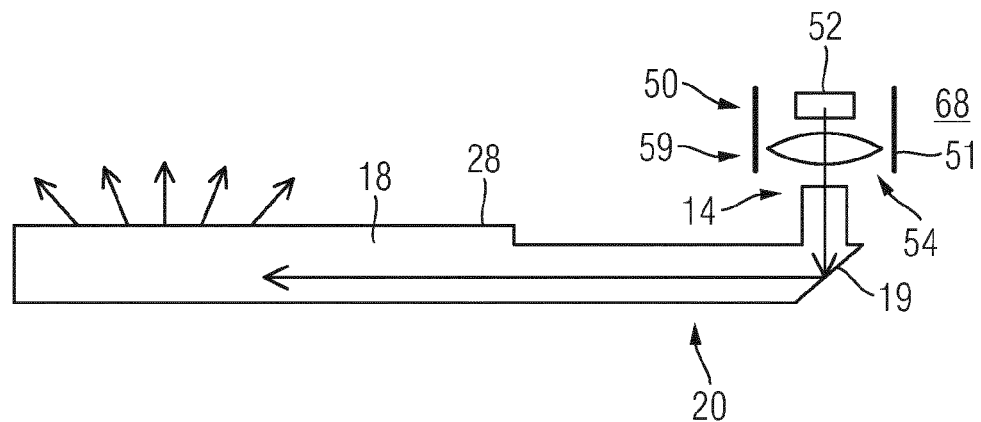
Fig. 5  A-A
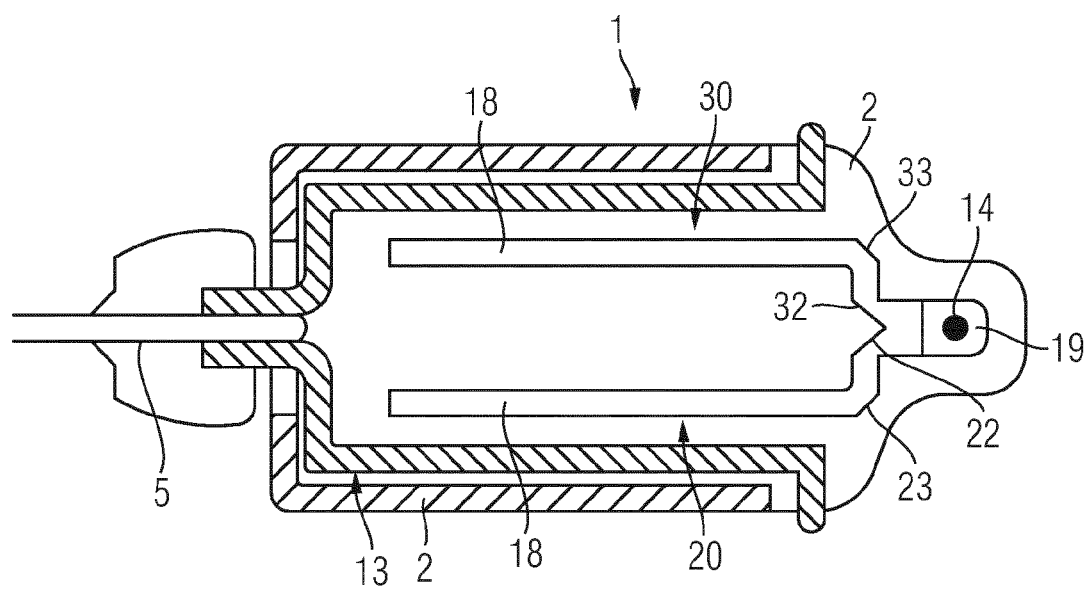
Fig. 6  B-B

SUPPLEMENTARY DEVICE FOR AN INJECTION DEVICE

CROSS REFERENCE TO RELATED APPLICATIONS

The present application is the national stage entry of International Patent Application No. PCT/EP2017/071596, filed on Aug. 29, 2017, and claims priority to EP Application No. 16186288.3, filed on Aug. 30, 2016, the disclosures of which are incorporated herein by reference.

TECHNICAL FIELD

The present disclosure relates to an apparatus for supplementing a medical device configured to eject or to inject a medicament.

BACKGROUND

A variety of diseases exist that require treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dose dial and observing the actual dose from a dose window or display of the insulin pen. The dose is then injected by inserting the needle into a suited skin portion and pressing an injection button or dose button of the insulin pen.

SUMMARY

The present disclosure relates to an apparatus for supplementing a medical device configured to eject or to inject a medicament. In particular, the present disclosure relates to a supplementary device for a manually operable injection device and further relates to a kit comprising a supplementary device and an injection device. The disclosure also relates to a method of monitoring the operation of a manually operable drug delivery device or injection device.

To be able to monitor insulin injection, for instance to prevent false handling of the insulin pen or to keep track of the doses already applied, it is desirable to measure information related to a condition and/or use of the injection device, such as for instance information on the injected insulin type and dose. In this respect, WO 2009/024562 discloses a medical device with a value sensor. There, a Radio Frequency Identification (RFID) unit comprises a value sensor such as a pressure sensor and is integrated with a liquid medicament container to enable wireless pressure or other medicament relevant parameter value monitoring. The liquid medicament container is coupled with a first housing part of the medical device, which first housing part may for instance constitute a pre-filled disposable injection device. The RFID unit communicates wirelessly with a control circuit that is contained in a second housing part of the medical device that is releasably attached to the first housing part. The control circuit is adapted to process the values measured by the RFID unit, to compare it with pre-defined values and to provide an alert to the user if the measured values fall outside normal operating conditions, and to communicate data relating to the measured values to an external device for further data processing.

Supplementary devices or accessory devices to be used with injection devices typically provide monitoring and recording of a dosing history. Supplementary devices are typically configured to collect data about injection times, duration of an injection procedure and so on. Supplementary devices are typically equipped with some electronic, rather costly and/or high quality components. Supplementary devices are intended to be used with a series of injection devices. The injection devices may be configured as disposable devices intended to be discarded after use or after a medicament contained therein has been used up. Manufacturing of disposable injection devices should be cost-efficient. In order to increase a level of user acceptance supplementary devices should also be rather compact and should exhibit an attractive design. Miniaturized supplementary devices may be producible at moderate costs. But with miniaturized injection devices illustration of captured or measured information or data may become difficult since there may not be enough space available on the supplementary device itself to visually indicate injection device-specific or medicament-specific information to a user.

It is therefore desirable to provide a supplementary device with a compact and attractive design and which is further capable to visualize injection- or device-specific information to a user in a convenient and intuitive way. The supplementary device should be further capable to provide handling instructions to a user of the device so that an overall device handling may become more intuitive and failure safe. When attached to the injection device the supplementary device should be capable to activate certain functions of the injection device. The supplementary device should complement the functionality of the injection device in terms of user interaction and user feedback. It is a further aim to provide an injection device to cooperate with the supplementary device. It is also an aim to provide a method of monitoring the operation of an injection device and to provide a visible feedback to a user prior, during or after completion of an injection procedure.

In one aspect of the present disclosure, a supplementary device is provided for an injection device, typically for a handheld and manually operable injection device. The supplementary device comprises a body attachable to a housing of the injection device. The body has at least a first portion facing towards the housing when attached to the housing of the injection device. The supplementary device further comprises at least one light source attached to the body. The supplementary device also has at least a first optical coupling located in or at the first portion. The optical coupling is connected to the at least one light source in a light transmissive way.

The first optical coupling is optically connectable to a second optical coupling that is arranged in or on the housing, typically in or at an outer surface of the housing. In this context the term 'optically connectable' means that the first and the second optical coupling are coupled to each other in a light transferring or light transmitting way. The first and the second optical couplings are connectable in terms of a transfer of light. For this, first and second optical coupling do not require to be mechanically connected. It is sufficient when first and second optical coupling are arranged at a certain distance but in a direct line of sight. In this way optical signals transmitted from the first optical coupling are receivable by the second optical coupling.

First and second optical couplings are arranged at specific and well-defined portions of the body of the supplementary device and of the housing of the injection device, respectively. The supplementary device is configured to be attached to the housing of the injection device in a well-defined way. When the body and hence the supplementary device is attached to the housing of the injection device in a predefined way the first optical coupling and the second optical coupling may face towards each other without any barrier in between. When the body is attached to the housing the first optical coupling and the second optical coupling are arranged in a common line of sight. They are directly optically coupled to each other. In this way optical signals transmitted from the first optical coupling can be received by the second optical coupling. Consequently, light generated by the at least one light source of the supplementary device can be transferred and coupled to the second optical coupling and hence to and/or into the injection device.

In this way the injection device void of an own light source can be provided with an illumination and with illuminating effects simply by attaching the supplementary device to the housing of the injection device and by establishing an optical connection between the first optical coupling and the second optical coupling. By means of the supplementary device the functionality of the injection device can be extended. The injection device can be provided with an illumination and with illuminating effects that may be used to assist and to guide operation and handling of the injection device. Due to the first and second optical couplings and the optical connection to be established therewith the injection device does not have to be equipped with a light source and/or with an electric energy source. Consequently, costs for manufacturing of the injection device can be kept at a rather low level and the injection device can be designed and configured as a disposable device with moderate or low production costs.

All optically active components for generating an illumination or various illuminating effects, such as a continuous or a blinking illumination, may be exclusively provided by the supplementary device. The injection device must be only provided at least with the second optical coupling, which may be a passive coupling that is configured to receive and, to guide, to scatter, to diffract or to reflect light. Generation of light may be exclusively provided by the supplementary device.

Due to the optical connection established by the first and the second optical couplings the overall size of an illuminated area on or in the housing of the injection device can be enlarged. The surface or the geometric expansion of an illuminated object or of an illuminated visual indicator provided on the injection device and optically coupled with the second optical coupling may exceed the geometric size of the supplementary device. In this way visual signals and visual information as well as an illumination and illuminating effects generated by the supplementary device can be displayed by and on the injection device on a comparatively large geometric scale. Simultaneously, the total size of the supplementary device can be kept in a rather low range thus increasing user acceptance to make use of the supplementary device and to improve the overall design of a kit comprised of the injection device and the supplementary device attached thereto.

In one embodiment of the present disclosure, the supplementary device comprises an electric energy source connectable to the at least one light source. The electric energy source may be connected, e.g. permanently connected to the at least one light source. The electric energy source may comprise a battery or a rechargeable battery. Since the supplementary device is equipped with both, a light source and with an electric energy source, any and all electrical components required to provide an illumination or an illuminating effect are provided by the supplementary device. Consequently, the injection device may be void of an electric energy source or some other power source. In this way, the injection device may be purely mechanically implemented. It may be void of any electrical component thus enabling to decrease the costs of production. Such a low cost injection device is particularly suitable as a disposable injection device.

In one embodiment, the supplementary device also comprises a processor connected to the at least one light source and being configured to control activation of the at least one light source. Of course, the processor is also configured to deactivate the at least one light source. Switching on and switching off as well as any kind of light modulation producible by the at least one light source is controllable by the processor. The processor may act and behave as a controller and may be configured to control the entire functionality of the supplementary device. The processor may comprise a microcontroller or a comparable central processing unit. The processor is connected to the electric energy source and is powered by the electric energy source. By arranging the processor in the supplementary device the injection device can be designed and configured to be void of a processor. In this way manufacturing and production costs for the injection device can be kept at a rather low level.

The processor is typically provided with a clock providing a time signal. In this way the processor is configured to record and to store information about a time and a date at which an injection procedure takes place. Moreover, the processor may be configured to determine and to measure the size of a time interval during which an injection or dose setting procedure takes place. The processor may be further configured to store the time and date information in conjunction with the amount of medicament dispensed. In this way the processor and the supplementary device is configured to store a dosing history.

In one embodiment, the supplementary device further comprises a sensor arrangement having at least one of an optical sensor, a temperature sensor and a microphone to detect or to measure at least one state parameter of the injection device. Depending on the type of implementation of the sensor arrangement the sensor arrangement is for instance configured to detect and to measure an actual configuration of the injection device, such as an idle or initial state, a state wherein a dose of a predefined or fixed size has been set or dialed, a state in which the injection device is conducting an injection procedure or a state in which the injection procedure has been completed.

The device configuration may be detectable by the optical sensor and/or by means of the microphone. By means of a temperature sensor a temperature of the medicament contained in the injection device and/or an ambient temperature can be measured. Based on a temperature measurement the processor can be provided with respective information in how far the medicament is stored or used in a recommended or admissible temperature range. If for instance the ambient temperature is above or below a predefined or admissible temperature for medicament injection the processor may generate a respective alert signal and may also activate the at least one light source to generate a respective visual alert signal. For instance, the light source may provide a red blinking or a flashlight to a user.

The injection device may be provided with a sound generator, such as a click sound generator that provides acoustic feedback prior, during and/or after completion of an injection procedure.

A characteristic and well-defined acoustic signal generated by the injection device may be recorded and detected by means of the microphone. When connected to the sensor arrangement the processor may process respective signals of the sensor arrangement. In this way and by means of an acoustic detection the processor is provided with information about an ongoing injection process or about termination of an injection process.

The sensor arrangement can be configured to generate electric signals to be analyzed and to be further processed by the processor. Electric signals generated by the sensor arrangement are indicative of an actual state of the injection device. When implemented as an electrically operated sensor arrangement the sensor arrangement is also connected and coupled to the electric energy source. It may be connected via the processor to the electric energy source. It may be the processor that activates or triggers the sensor arrangement to initiate detecting or measuring of the at least one state parameter of the injection device. In addition or alternative, the sensor arrangement may further comprise piezoelectric sensors, force sensors, pressure sensors as well as capacitive sensors or magnetic sensors.

In one embodiment, the supplementary device comprises a wireless communication interface to communicate with an external electronic device. The wireless communication interface is configured to transceive electromagnetic radiation and respective electromagnetic signals. The wireless communication interface is configured to broadcast as well as to receive electromagnetic signals. Electromagnetic signal transmission may be based on conventional wireless transmission standards, such as IEEE 802.11, i.e. the WLAN standard, the NFC standard, infrared communication protocols, Bluetooth communication standards or RFID communication protocols, just to mention a few.

By means of the wireless communication interface a comprehensive data and signal exchange may take place between the supplementary device and the external electronic device. Data processing may be conducted not only by the supplementary device and the processor thereof but also by the external electronic device. The external electronic device may comprise a portable electronic device, such as a smartphone, a tablet computer, a smart watch or any other type of a computer device. Such external electronic devices are nowadays widely distributed and are intensively used by a large group of users. By implementing a specific software, such as an app on the external electronic device data and signal transmission with the supplementary device may take place.

A graphic representation as well as a comprehensive analysis of gathered data may be provided by and on the external electronic device. Respective functionalities of the supplementary device and the functionality of the processor of the supplementary device can be kept on a rather low level. The processor of the supplementary device may be limited to signal recording and acquisition of signals received from the sensor arrangement. The processor of the supplementary device may be further limited to transfer, to store and/or to buffer recorded electronic signals obtained from the sensor arrangement. A processing and analysis of data provided by the sensor arrangement may be conducted by the external electronic device after respective signals have been received from the supplementary device.

According to a further embodiment, the supplementary device is void of a display. Due to the wireless communication with the external electronic device the supplementary device does no longer require an own display. Typically, the external electronic device is equipped with a display by way of which any kind of data or processed data collected and/or derived from the sensor arrangement can be provided to a user in a rather attractive and intuitive way. Providing a display only with the external electronic device enables and offers a further miniaturization of the supplementary device.

Alternatively or in addition, the optical connection between the supplementary device and the injection device may also provide some kind of display functionality. Any passive optical element of the injection device coupled to the second optical coupling may provide some kind of display functionality. The passive optical element of the injection device may provide a certain color or different colors as well as a continuous or blinking illuminating effects when optically coupled to the at least one light source of the supplementary device attached to the housing of the injection device.

In an embodiment, the supplementary device comprises at least one mechanical connector to releasably engage with a correspondingly-shaped mechanical connector of the housing. The mechanical connector of the supplementary device may be attached to or may be integrated into the body of the supplementary device. The mechanical connector may comprise a snap feature, such as a hook to engage with a correspondingly-shaped recess, e.g., in the housing of the injection device. It is also conceivable that the housing of the injection device is provided with a snap feature or with a hook to engage with a correspondingly- or complementary-shaped recess in the body of the supplementary device.

The mechanical connectors of the supplementary device and the injection device are not limited to positively engaging connectors. The mechanical connectors of the supplementary device and the injection device may be implemented to provide a frictional engagement of the supplementary device and the injection device. Typically, the mechanical connectors of the supplementary device and the injection device are located and arranged at predefined portions of the body and the housing. The location and the geometry of the mutually engaging mechanical connectors of the body and the housing provide a well-defined attachment configuration of the supplementary device to the housing.

When attached and fixed to the housing the body of the supplementary device is arranged such that the first optical coupling and the second optical coupling establish and form an optical connection so that visual signals generated by the at least one light source are transferrable from the first optical coupling to the second optical coupling and hence across the optical connection or optical interface between the supplementary device and the injection device.

In an embodiment, the supplementary device further comprises at least one visual indicator that is connected to the processor to visually indicate a momentary state of the injection device. The visual indicator may comprise another light source of the supplementary device. Alternatively, the at least one light source of the supplementary device may be visible from outside the supplementary device so that the at least one light source optically coupled with the first optical coupling also provides at least one visual indicator of the supplementary device. In this way the supplementary device itself is capable to provide an illumination or an illuminating effect. The supplementary device may hence provide a visual information to a user even when not connected to the injection device or when improperly connected to the injection device.

The visual indicator may be useful to indicate to a user that the supplementary device is properly attached or aligned with the injection device. The at least one visual indicator of the supplementary device may further provide information about the status of the supplementary device itself. The visual indicator may be used to visually indicate to a user that the electric energy source is empty or full, that a data transmission with the external electronic device should take place or that such data transmission is actually in progress or that data transmission has been completed successfully or unsuccessfully.

In addition the at least one visual indicator may also provide information about the state parameter of the injection device that has been determined or measured by the sensor arrangement. The visual indicator of the supplementary device may further provide assistance to a user to properly attach the supplementary device to the injection device and to properly conduct operation of the supplementary device and/or of the injection device.

In an embodiment, the at least one light source comprises a multi-color illuminant or wherein the at least one light source comprises several illuminants of different color. Typically, the at least one light source comprises at least one light emitting diode (LED). The LED or the light source in general may be configured to provide differently colored optical signals or light beams in the visual spectral range. When the illuminant or illuminants of the light source are implemented as a single color illuminant there are provided several illuminants each of which having a different color and each of which being configured to produce and to generate visible optical signals of a different wavelength or spectral range.

In this way differently colored optical signals generated by the at least one light source may be directly and intuitively indicative of a momentary status of the supplementary device and/or of the injection device. For example, a red color may represent some kind of alert or warning. A green color may represent a successful preparation or completion of a dose setting procedure and/or dispensing procedure of a dose of the medicament.

Not only the at least one light source but also the visual indicator may comprise a multi-color illuminant or several illuminants of different color.

In another aspect, an injection device for dispensing of a dose of a medicament is provided. The device comprises a housing to accommodate a cartridge filled with a medicament and sealed with a piston towards a proximal end. The cartridge typically comprises a barrel, e.g., a cylindrically-shaped vitreous barrel. The piston is then slidably displaceable along the cylinder long axis of the barrel. By a displacement of the piston towards a distal end of the cartridge a medicament contained inside the cartridge can be expelled via a distal dispensing end thereof.

The injection device further comprises a drive mechanism comprising at least a plunger or a piston rod to operably engage with the piston of the cartridge in order to expel a dose of the medicament via the distal end of the cartridge. The injection device further comprises at least one indicator attached to or arranged inside the housing. The at least one indicator is visible from outside the housing. The injection device also comprises at least a second optical coupling as already mentioned above. The second optical coupling is arranged in or on the housing. It is connected to the at least one indicator in a light transmissive way.

The injection device, in particular its housing and the second optical coupling are particularly configured to mate and to interact with the supplementary device as described above. The housing of the injection device is configured to releasably engage with the supplementary device, in particular with the body of the supplementary device. When engaged with the supplementary device the first optical coupling of the supplementary device forms an optical connection with the second optical coupling of the injection device. In this way an illumination or an illuminating effect producible by the at least one light source of the supplementary device can be transferred and optically guided to the at least one indicator of the injection device. The injection device may be implemented all mechanically. It may be void of any electronic or light generating components. The injection device may only comprise at least one passive optical component featuring the at least one indicator and the second optical coupling.

Since the injection device may be void of electronic or active optical components the costs for manufacturing and producing the injection device can be kept at a rather low level which is of particular benefit when the injection device is configured and designed as a disposable device.

Typically the injection device is readily equipped with the cartridge that is filled or prefilled with the medicament. Having arranged the cartridge inside the housing of the injection device enables the possibility to provide an injection device ready to use to an end user. Only a minimum of preparation steps may have to be conducted, such as a priming procedure before an injection may take place with the help of the injection device.

In one embodiment, the injection device comprises at least one light conductor arranged inside the housing and has a first end provided with the second optical coupling. The at least one light conductor may have a second end forming the at least one indicator. The at least one light conductor may integrate the second optical coupling and the at least one indicator in a single passive optical element. One end thereof is particularly configured to receive an optical signal, hence a light beam from the supplementary device and from the first optical coupling thereof.

Light entering the at least one light conductor via the second optical coupling may be conducted and transferred to a portion of the light conductor that serves and behaves as the at least one indicator. The at least one indicator, hence the second end or a particular geometric section of the at least one light conductor may be located remote from the second optical coupling. When arranged to or inside the housing of the injection device it is particularly the second optical coupling that extends through a sidewall portion of the housing. In this way at least the second optical coupling is accessible from outside the injection device. When attaching the supplementary device to an outer surface or to the outer circumference of the housing of the injection device the first optical coupling and the second optical coupling may be arranged in a direct line of sight.

At least a portion of the at least one light conductor may be covered by the housing of the injection device. The second end of the at least one light conductor and/or the at least one indicator is typically located either at an end section of the housing, in a window section of the housing or in an aperture formed in the housing. In this way at least the second end of the light conductor and/or the at least one indicator is visible from outside the housing.

In an embodiment, the housing comprises at least one through opening, typically in a sidewall portion. At least one of the second optical coupling and the at least one indicator is arranged inside the through opening or extends into the through opening. The second optical coupling may flush with an outer surface of the housing of the injection device. In some embodiments the second optical coupling may even protrude from the housing. In other embodiments it may be located inside a recessed portion of the housing and may be recessed with regard to the outer surface of the housing.

It is generally conceivable that the second optical coupling also coincides or provides a mechanical connector of the housing to releasably engage with a correspondingly-shaped mechanical connector of the supplementary device, in particular of the body of the supplementary device. In this regard also the first optical coupling may coincide or may form a mechanical connector of the supplementary device. In such an embodiment the first and second optical couplings may provide a double function. They may provide optical light and optical signal transmission as well as a mechanical connection between the supplementary device and the injection device.

The at least one indicator is typically provided along or inside a window of the housing of the injection device. Such a window is typically provided in a sidewall portion of an, e.g., cylindrical housing of the injection device. Depending on the specific implementation the at least one indicator may even cover the window or a portion thereof. The at least one indicator may comprise a transparent or translucent material, such as a transparent or translucent thermoplastic material. Additionally or alternatively, the at least one indicator may extend along a border or a side edge of the at least one through opening of the housing or of a respective window of the housing. The at least one indicator may provide an illuminating frame of the through opening or of a window of the housing. There may be several through openings in the housing that may be equipped with several and with different indicators all optically connected to a single second optical coupling or to a plurality of second optical couplings that are individually connectable with a respective number of first optical couplings.

Providing a multiplicity of first and second optical couplings to be optically connected pair wise a plurality as well as different optical signals may be provided simultaneously and/or concurrently. In this way an information density of visual signals generated and provided by the interaction of the injection device and the supplementary device can be increased.

In an embodiment the at least one indicator comprises a frosted or roughened surface. By means of a frosted or roughened surface or surface section a rather distinct and significant illumination and/or a respective illuminating effect can be provided even on the basis of a comparatively low intensity of an optical signal. With a frosted or roughened surface a light beam guided through the at least one light conductor will experience a widespread angular scattering or diffraction that is clearly visible for a user and independent of a relative angle between an orientation of the injection device and a viewing direction of the user.

According to an aspect, there is provided a kit including an injection device as described above and further including a supplementary device as described above. Here, the supplementary device is attachable to the housing of the injection device in such a way that the first optical coupling of the supplementary device and the second optical coupling of the injection device form an optical connection or an optical interface configured for transmitting light generated by the light source of the supplementary device to the at least one indicator of the injection device.

In this way the injection device may be equipped and supplemented with an illumination or with illuminating effects without the necessity to provide the injection device with an own light source and/or with an electric energy source.

In addition, the comparatively large geometric expansion of the injection device compared to the rather compact supplementary device can be used for a rather comprehensive, clear and intuitive assisting of a user of the device through the process of dose setting and/or dose dispensing. The supplementary device may be void of an own display and may be also void of an own visual indicator. The task of providing visual information to a user may be completely provided by the injection device thus enabling a further miniaturization of the supplementary device.

In an aspect also a method of monitoring the operation of an injection device is provided. The method comprises the steps of attaching a supplementary device as described above to a housing of an injection device as described above. In a further step the supplementary device is activated. Once activated, the supplementary device is configured to detect or to monitor for a momentary state or configuration of a drive mechanism of the injection device. If and when the injection device is used for setting and/or for dispensing of a dose of a medicament a perspective movement, actuation or configuration of the drive mechanism can be detected and/or monitored by the supplementary device. The dose setting and/or the dose dispensing may be optionally recorded, tracked and logged by the supplementary device. Moreover the method is configured to generate a visible feedback by means of the light source of the supplementary device and to transmit via an optical connection of the first optical coupling with the second optical coupling the visible feedback to the at least one indicator of the injection device. Here, the supplementary device is configured to generate a visible feedback, which feedback is indicative of the momentary state or configuration of the drive mechanism. The visible feedback is typically provided by means of the light source of the supplementary device.

The at least one light source of the supplementary device is configured to generate at least one visual optical signal prior, during or after one of a dose setting procedure and a dose dispensing procedure. Due to the attachment of the supplementary device to the injection device and due to the optical connection formed by the first and second optical couplings the visual signal generated by the supplementary device is optically transferred and optically guided to the at least one indicator of the injection device. Such a method of monitoring and providing of a visible user feedback may enhance general user acceptance of the injection device and of the supplementary device to be attached thereto. In addition to that the overall design and attractiveness of the injection device and of the supplementary device may be enhanced.

It is further to be noted that structural and functional features of the supplementary device, of the injection device and of the kit equally apply to the method of monitoring the operation of the injection device and to the method of providing user assistance and/or user feedback; and vice versa.

BRIEF DESCRIPTION OF THE DRAWINGS

In the following, embodiments of the present invention will be described by making reference to the drawings, in which:

FIG. 5 is a cross-section view along A-A of FIG. 2, illustrating the optical connection between first and second optical couplings, FIG. 6 is a cross-section view along B-B of FIG. 2.

DETAILED DESCRIPTION

Figure 10:
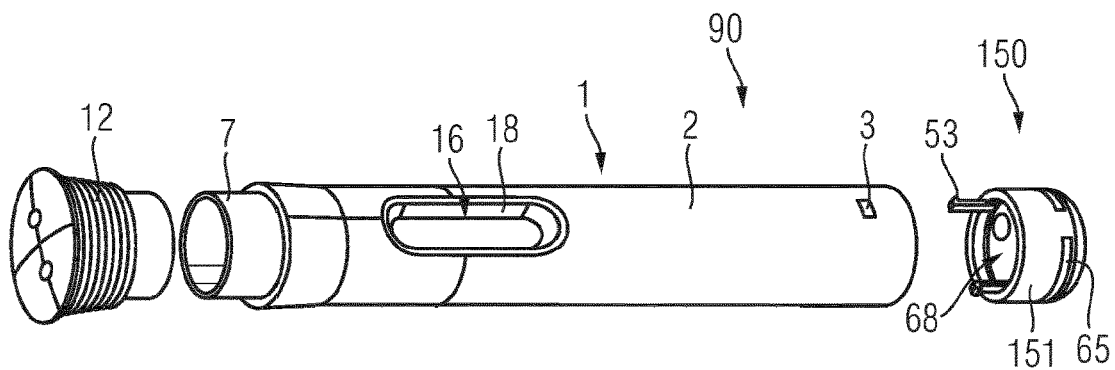
FIG. 10 is a schematic perspective view of an embodiment of the injection device.
Figure 11:
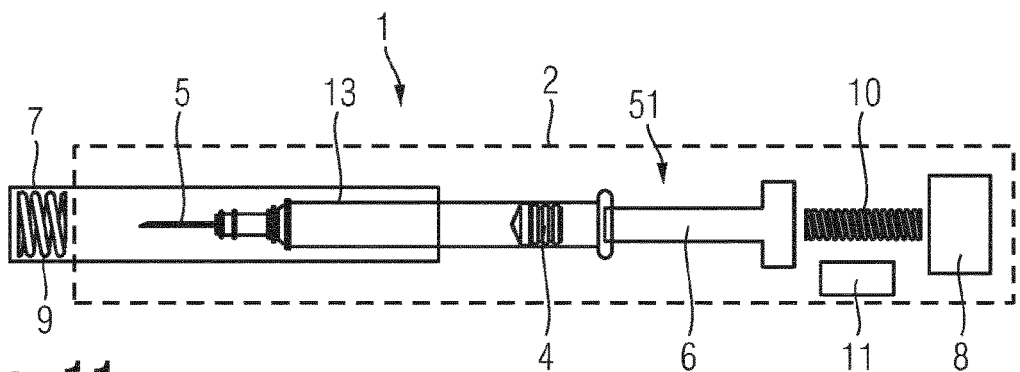
FIG. 11 is a schematic representation of various components of the injection device.
Figure 12:
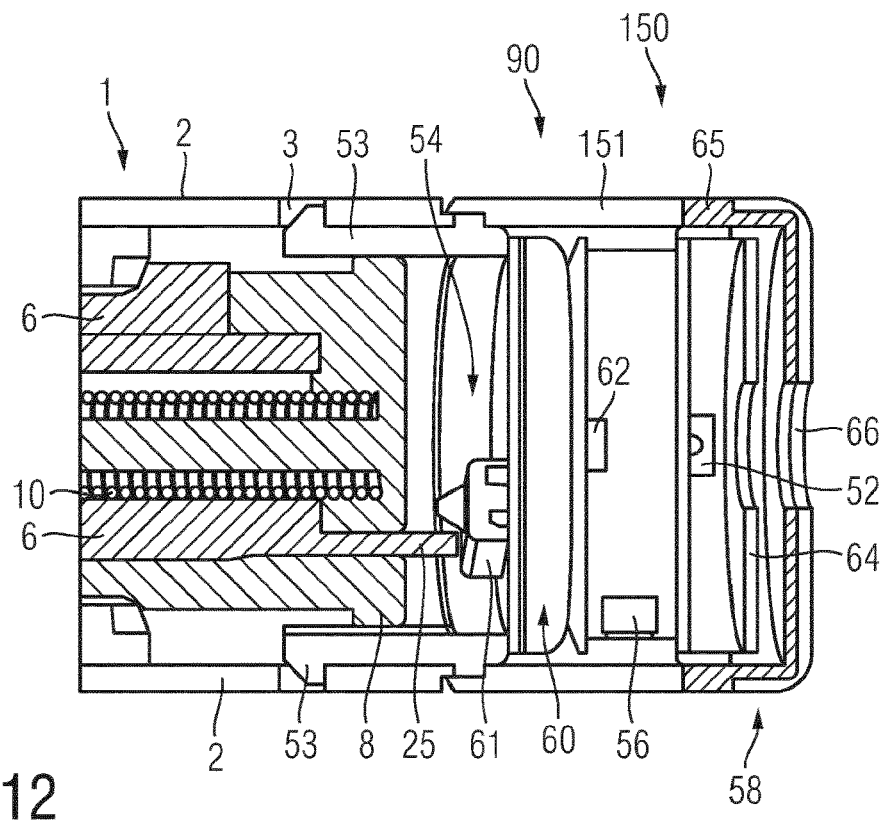
FIG. 12 is a longitudinal cross-section through a proximal end of the injection device connected to the supplementary device.
Figure 13:
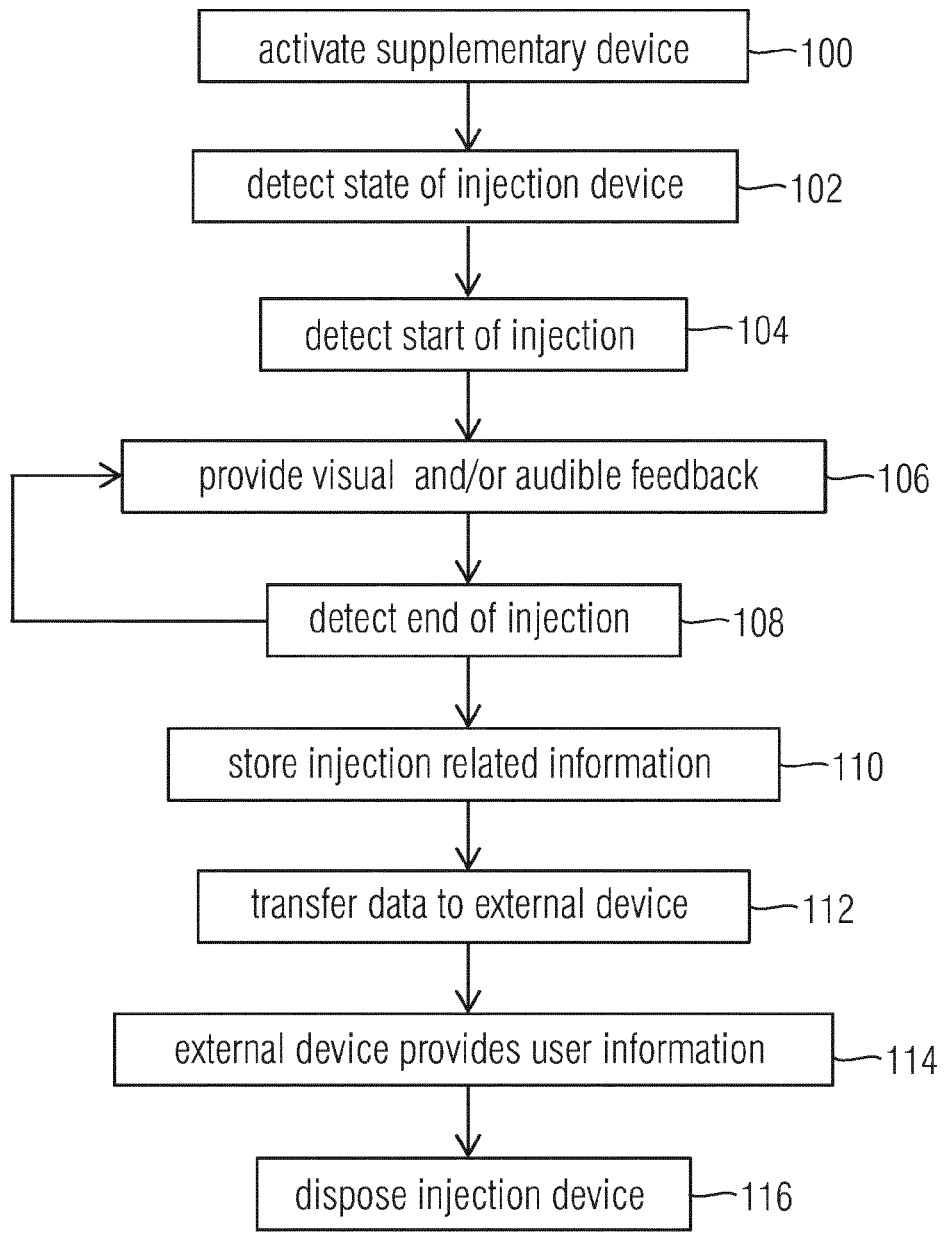
FIG. 13 is a flowchart of a method of monitoring operation of the injection device and of providing feedback to a user.

The injection device 1 as schematically illustrated in FIGS. 1-4 and in FIGS. 10-12 comprises an elongated housing 2 that is of substantially cylindrical shape. The housing 2 is configured to accommodate a cartridge 13 filled with a liquid medicament and to accommodate a drive mechanism 15 that is configured to at least dispense a dose of the medicament contained inside the cartridge 13. The cartridge 13 comprises a cylindrically-shaped barrel, e.g. a vitreous barrel. Towards a proximal end the cartridge 13 is sealed by a piston 4, typically made of an elastomeric material, such as rubber. A distal end of the cartridge 13 is connectable with a piercing element, e.g. with a needle 5. The needle 5 is typically configured as an injection needle.

A proximal end of the needle 5 is located inside an interior volume of the cartridge 13 filled with the liquid medicament. A distal end of the needle 5 is tipped so as to pierce biological tissue in order to deliver a dose of the liquid medicament into the pierced tissue. The drive mechanism 15 comprises at least an elongated plunger 6 by way of which the piston 4 is displaceable towards a distal direction, hence towards the needle 5 attached to the cartridge 13. An advancing motion of the plunger 6 is typically controllable and can be initiated by the drive mechanism 15. In the embodiment as illustrated in FIGS. 10 and 11 the injection device 1 is configured as a fixed dose injection pen that is suitable for delivering a single predefined dose of a medicament. The injection device 1 may be configured as a so-called auto injector such as for instance described in more detail in EP 2 823 841 A1, the entirety of which being incorporated herein by reference.

The device 1 comprises a shroud 7 of sleeve-like shape. The shroud 7 is operable coupled to the plunger 6. The injection device 1 is further equipped with a protective cap 12 that serves to cover a distal end of the injection device 1. Prior to administering of a dose of the medicament the protective cap 12 has to be detached from the housing 2 so as to expose the dispensing end of the injection device 1 for conducting the dispensing procedure as indicated in FIG. 11. When the cap 12 is removed the shroud 7 is in a first extended position relative to the housing 2, protruding from the housing 2 in a distal direction. When the injection device 1 is pressed against an injection site, the shroud 7 translates proximally relative to the housing 2 against a biasing force of a shroud spring 9. The shroud spring 9 is inserted into the shroud 7, and the shroud 7 with the shroud spring 9 is inserted into a distal section of the housing 2.

When the shroud 7 translates proximally from the first extended position to a retracted position a shroud rib (not illustrated) engages a plunger rib (not illustrated) to rotate the plunger 6 from a first rotational position to a second rotational position. When the plunger 6 is in the second rotational position it is free to translate axially under the force of a drive spring 10.

The advancing motion of the plunger 6 may be triggered and provided by a drive spring 10. The drive spring 10 may be supported and may be in abutment with an insert 8 that is rigidly connected to the housing 2 of the injection device 1. Optionally, the injection device 1 is further equipped with a click sound generator 11 that is configured to generate an audible and characteristic sound, e.g. when a dispensing procedure is in progress and/or when a dispensing procedure has terminated or is about to terminate.

The injection device 1 further comprises a through opening 16 that may be configured as an inspection window through which a state of the injection device 1 is visible. Inside the through opening 16 or window at least some kind of indicator may be visible to a user. The indicator may comprise numbers, symbols or simply a particular color sheet thus indicating whether the injection device 1 is ready to use, if a dose of a particular size has been set, if and in how far a dose setting procedure and/or a dose dispensing procedure is currently in progress and/or if a dose dispensing action has terminated or is about to terminate.

The through opening 16 may be formed as an aperture in a sidewall of the housing 2.

Alternative to an implementation as an auto injector the injection device 1 may be implemented as a manually operable and all mechanically implemented injection device 1 that provides individual setting of doses of different sizes and subsequent dispensing thereof. Alternative to the illustrated embodiment the injection device 1 may also comprise a rotatable dose dial and/or a dose button located at a proximal end of the housing 2 and being depressible in distal direction so as to trigger and to control a dose dispensing or dose injection procedure.

Figure 1:
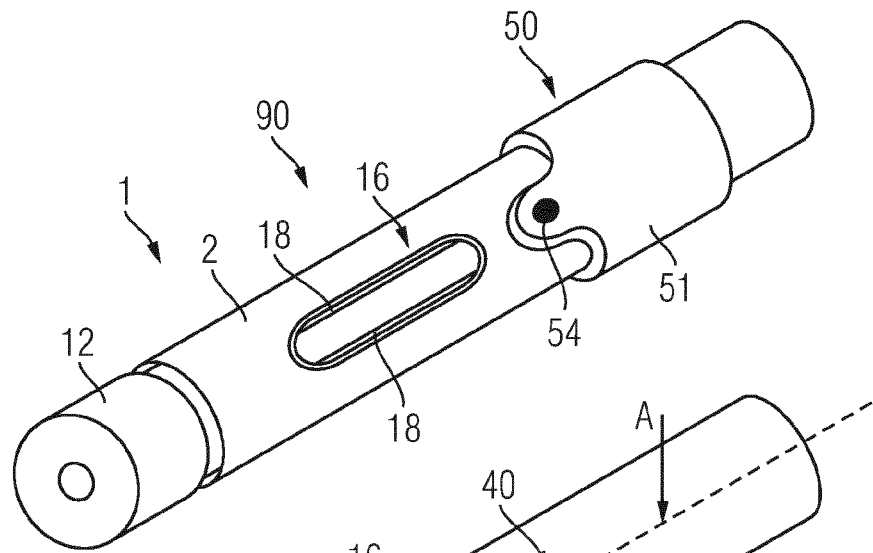
FIG. 1 is a schematic view of a kit including an injection device and a supplementary device attached thereto.

The kit 90 as illustrated in FIGS. 1 and 10 further includes a supplementary device 50, 150 that is attachable to the housing 2 of the injection device 1. The supplementary device 50, 150 comprises a body 51, 151 that may be of sleeve-like or knob-like shape. The body 51 as illustrated in FIG. 1 comprises a hollow shape so as to enclose an outer surface or outer circumference of the housing 2. In such a geometric configuration the body 51 may be slipped over the housing 2 of the injection device 1. In the other illustration according to FIGS. 10 and 12 the supplementary device 150 is configured as a longitudinal extension of the elongated housing 2. Here the body 151 comprises an outer circumference that flushes with the outer circumference of the housing 2. Here, the body 151 comprises two geometrically oppositely located and longitudinally extending mechanical connectors 53 to mate and to engage with correspondingly-shaped mechanical connectors 3 of the housing 2 of the injection device 1.

As illustrated in FIGS. 8-10 and 12 the mechanical connectors 53 comprise longitudinally extending snap arms that protrude in distal direction from the cylindrically-shaped body 151. The mechanical connectors 53 comprising a snap feature or a hook at a distal end may slide along an inside facing portion of the sidewall of the housing 2 when the supplementary device 150 is attached to the housing 2. Upon reaching an assembly configuration the mechanical connectors 53 snap into correspondingly-shaped mechanical connectors 3 of the housing. Here, the mechanical connectors 3 are configured as recesses in the sidewall of the housing 2 that match in shape and position with the snap features or hooks of the mechanical connectors 53. In this way a releasable and positively engaging mechanical connection between the supplementary device 150 and the injection device 1 is provided.

The supplementary device 50, 150 comprises at least one sensor arrangement 60. In the embodiment as illustrated in FIG. 12 the sensor arrangement 60 comprises an optical sensor 61, such as a photodiode and a temperature sensor 62. In the configuration of the injection device 1 as illustrated in FIG. 12 the plunger 6 is in its undeployed and initial configuration. The plunger 6 comprises an extension 25 that protrudes in proximal direction from the end of the plunger 6 and which extends through the insert 8 of the injection device 1. In other words the extension 25 is visibly detectable at a proximal end of the housing 2. The optical sensor 61 is particularly configured to detect whether the extension 25 and hence whether the plunger 6 is located in an initial position.

When at least one of a dose setting procedure and a dose dispensing procedure is triggered the plunger 6 advances in distal direction and hence the extension 25 separates from the optical sensor 61. The optical sensor 61 may sense the distally directed displacement of the extension 25 and hence of the plunger 6. Since the optical sensor 61 and the entire sensor arrangement 60 is connected to a processor 56 of the supplementary device 150 and since the processor 56 is equipped with a clock a timestamp can be generated and hence a point of time at which a dispensing procedure took place can be recorded and/or logged.

Alternative to an implementation as an optical sensor 61 the sensor for detecting the actual position of the extension 25 may be also implemented by a magnetic sensor, by a switch, by a resistive sensor and/or by a capacitive sensor. In general, the sensor arrangement 60 is configured to monitor or to detect the momentary state or configuration of the drive mechanism 15 of the injection device 1. Insofar, the sensor arrangement 60 enables generation of a visible feedback signal being indicative of e.g. a momentary state or configuration of at least one of the drive mechanism 15, the plunger 6 or being indicative of environmental conditions the supplementary device or the injection device are exposed to.

Figure 7:
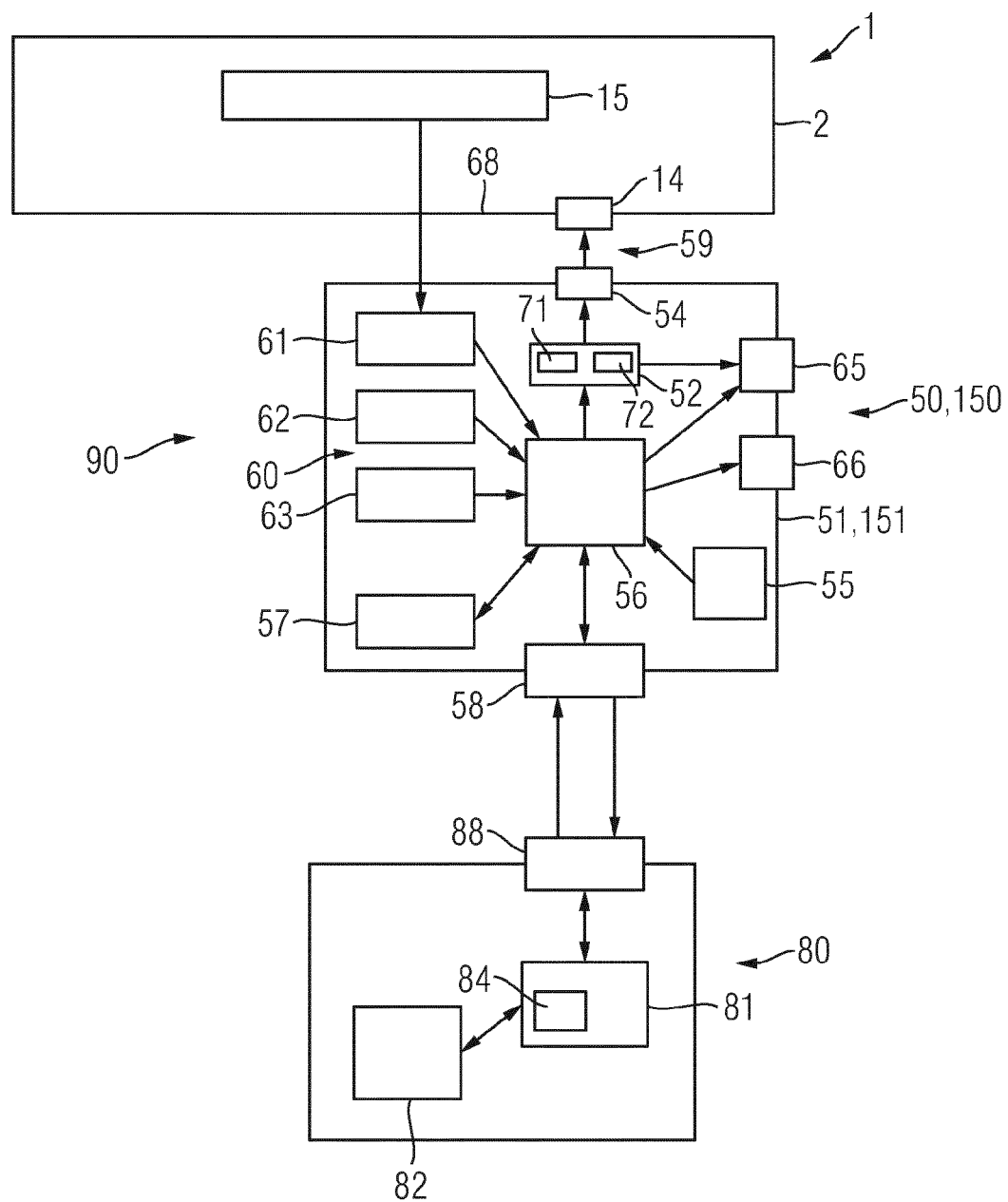
FIG. 7 depicts a block diagram of the interaction of the supplementary device with the injection device and further with an external electronic device.

Additionally, the sensor arrangement 60 comprises a temperature sensor 65 that is configured to measure the ambient temperature. The temperature sensor 65 is also connected to the processor 56 as illustrated in FIG. 7 so as to provide actual temperature information to the processor 56. The processor 56 is hence configured to record and to log an actual temperature as well as a temperature profile and hence a temperature history. In this way the processor 56 may track and control if the injection device 1 is stored within a predefined temperature range The supplementary device 150 is further equipped with a communication interface 58 that is also connected to the processor 56. By means of the communication interface 58 a wireless signal transmission and data transmission can be established with an external electronic device 80, such as a smartphone, a smart watch or a tablet computer. In the embodiment as illustrated in FIG. 12 the communication interface 58 comprises an antenna 64, e.g. a NFC antenna. The supplementary device 50 may optionally also comprises at least one light source 52, typically implemented as a LED, in particular as a multi-color LED.

The light source 52 is also connected to the processor 56. Depending on a measured or detected state of the injection device 1 and/or depending on a measured or detected environmental condition, such as the temperature the processor 56 may trigger an activation of the light source 52 so that a particular visually perceivable signal is generated by the light source 52. The processor 56 and the sensor arrangement 60 might be configured to generate a visible feedback e.g. by means of the light source 52 depending on the momentary state or configuration of the drive mechanism 15 of the injection device 1. Visual signals generated by the light source 52 may be directly visible on the supplementary device 150. As illustrated in FIGS. 8-10 and 12 the body 51 of the supplementary device may comprise at least one indicator 65, 66. Here, the indicator 65 is a slit or an aperture in a sidewall of the body 151. The visual indicator 66 is a through opening or orifice in an end wall of the body 151.

Both or only one of the visual indicators 65, 66 may be filled with a transparent medium, such as a light guiding transparent or translucent plastic material. The transparent material may completely fill the through opening in the body 151 forming the visual indicator 65, 66. The visual indicator 65, 66 and hence the material located and filling the respective through opening may flush with the outer surface of the body 151. Any activation of the light source 52 will be directly visible via the visual indicators 65, 66 of the supplementary device 150.

The injection device 1 is particularly configured as a disposable device and the supplementary device 50, 150 is configured to be releasably attached to a series of injection devices 1. Once the medicament located inside the injection device 1 has been used up or should no longer be used the supplementary device 50, 150 may be detached from the housing 2 of the injection device 1 and may be reattached to another, typically a new injection device 1. In this way a medication and dosing history conducted with a series and with multiple injection devices 1 may be recorded and logged by a single supplementary device 50, 150. Hence, the supplementary device 50, 150 is configured and designed as a reusable device. It can be used over a rather long term or time interval and may hence comprise high quality electronic components.

In the block diagram of FIG. 7 the interaction of the supplementary device 50, 150 with the injection device 1 and with the external electronic device 80 is schematically illustrated. The sensor arrangement 60 of the supplementary device 50, 150 may not only comprise an optical sensor 61 and a temperature sensor 62 but also a microphone 63 or some other type of sensor, such as a capacitive sensor, a resistive sensor, a switch or a magnetic sensor. When comprising a microphone 63 the supplementary device 50, 150 is adapted and configured to record and to track a characteristic sound, e.g. a clicking noise produced by a click sound generator 11 of the injection device 1. In this way the supplementary device 50, 150 may also provide an acoustic monitoring and acoustic surveillance of the injection device and the handling thereof.

The supplementary device 50, 150 may optionally comprise a storage 57 connected to the processor 56. The storage 57 is configured to store or to buffer electric signals generated or processed by the processor 56. Sensor signals as well as data derived therefrom may be locally stored in the storage 57, in particular in such circumstances where a signal transmission and data connection to the external electronic device 80 is not available. The supplementary device 50, 150 is further equipped with an electric energy source 55, typically in form of a battery or a rechargeable battery. The processor 56 further controls activation of the at least one light source 52. As illustrated in FIG. 7 the light source 52 may comprise several illuminants 71, 72 of different color. The indicators 65, 66 may be coupled to the at least one light source 52 in a light transmissive way. Alternatively, the visual indicators 65, 66 of the supplementary device 50, 150 may be provided with an own light source.

As illustrated in FIG. 7 the external electronic device 80 also comprises a processor 81 on which a particular software 84, typically in form of an app is running. The processor 81 is further connected with a display 82 and/or with a speaker so as to provide vast and comprehensive communication with the user. The external electronic device 80 further comprises a wireless communication interface 88 by way of which a data exchange with the wireless communication interface 58 of the supplementary device 50, 150 can take place. Due to the wireless data transmission between the external electronic device 80 and the supplementary device 50, 150 the display 82 of the external electronic device 80 can be exclusively used to visualize measured or detected parameters or data of the injection device 1. In this way the supplementary device 50, 150 may be void of an own display. The wireless data transmission with the external electronic device 80 enables a further miniaturization of the supplementary device 50, 150.

Figure 8:
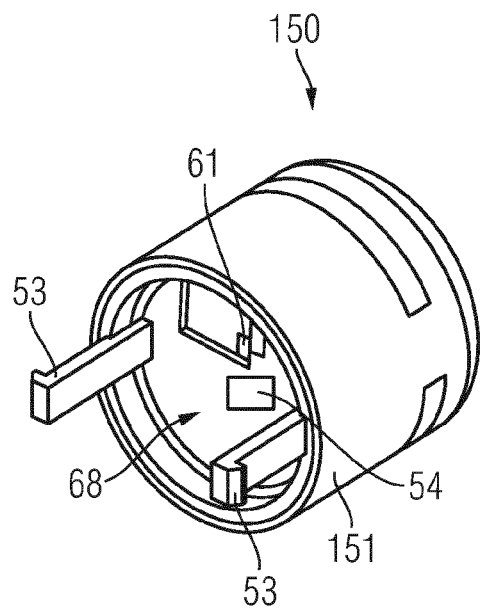
FIG. 8 is a perspective view of an embodiment of the supplementary device.
Figure 9:
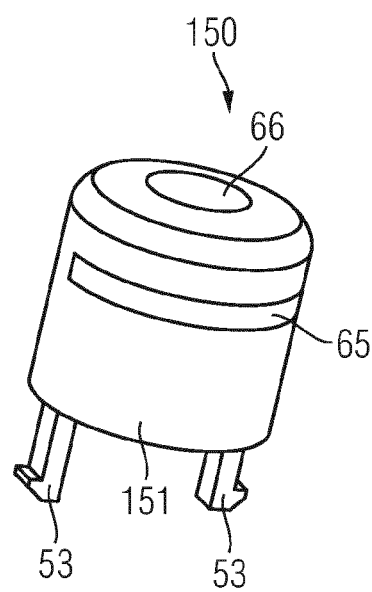
FIG. 9 is another perspective view of the supplementary device.

Furthermore, the supplementary device 50, 150 comprises a first optical coupling 54 to cooperate and to be optically coupled with a second optical coupling 14 provided at or in the housing 2 of the injection device 1. The first optical coupling is provided at or in portion 68 of the body 51, 151 that faces towards an outer surface of the housing 2 of the injection device when attached thereto. The portion 68 of the body 51 may be located at a radially inwardly facing sidewall section of a ring shaped or annular shaped body 51 as shown in FIG. 1. The portion 68 provided with the first optical coupling 54 may be also designed or configured as an end wall, e.g. a distal end wall of the body 151 as shown in FIG. 8.

When attached to the housing 2 of the injection device 1 the first optical coupling 54 is in a direct line of sight with the second optical coupling 14 so as to form and to establish an optical connection 59 between the housing 2 and the body 51, 151 and hence between the injection device 1 and the supplementary device 50, 150. The optical connection 59 and the light transmitting coupling of the first and the second optical couplings 54, 14 provides the possibility to generate illumination and illuminating effects directly on the injection device 1 without the necessity to implement a light source directly in or at the injection device 1. Instead, all light generating components as well as an electric energy source 55 are exclusively provided and contained in or at the supplementary device 50, 150. By attaching the supplementary device 50, 150 to the injection device 1 in a light transmitting way and by establishing the optical connection 59 light signals or an illumination generated by or in the supplementary device 50, 150 can be transferred to the injection device 1.

Figure 2:
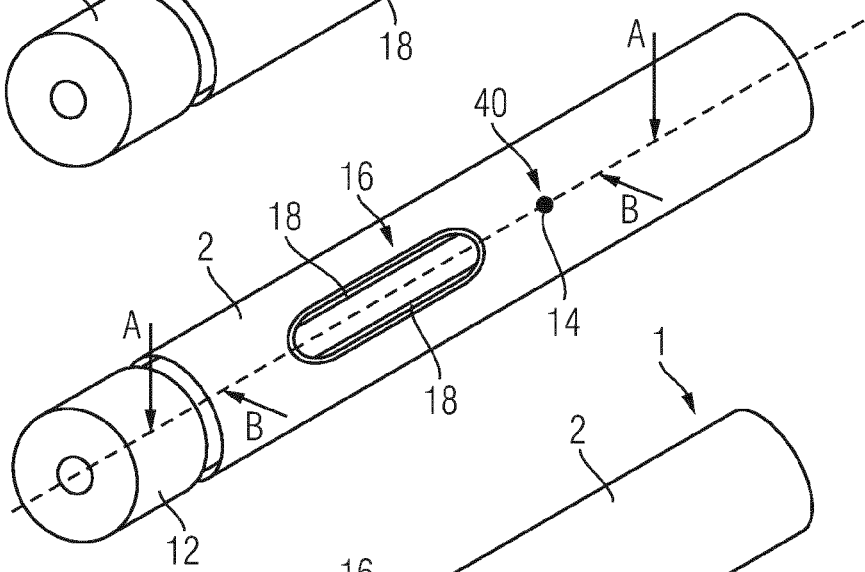
FIG. 2 is a view of the injection device of FIG. 1 without the supplementary device.
Figure 3:
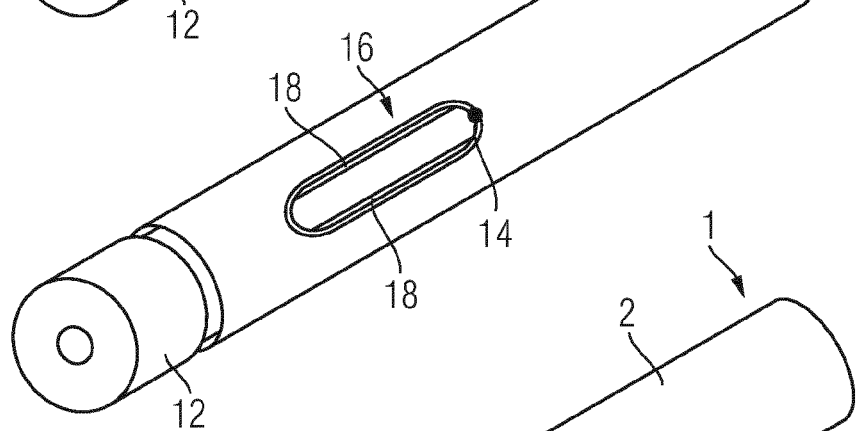
FIG. 3 is an illustrative drawing of another embodiment of the injection device.
Figure 4:
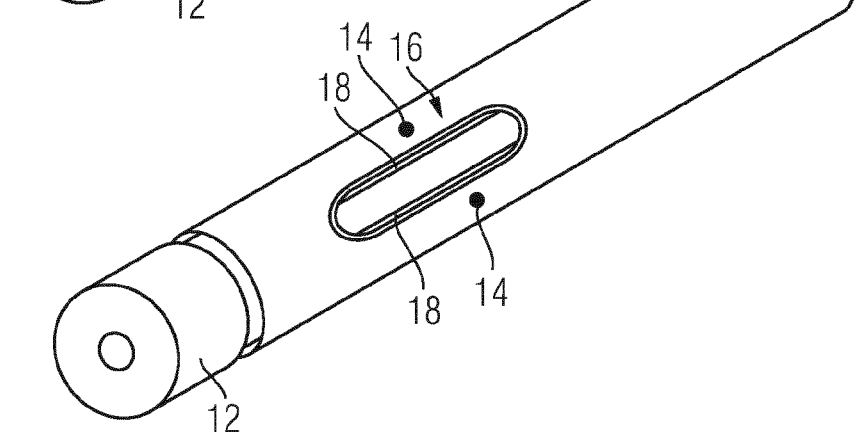
FIG. 4 is a perspective view of another embodiment of the injection device.

The second optical coupling 14 is typically provided in a through opening 40 of the housing 2. As shown in FIGS. 2-4, the second optical coupling 14 located inside and reaching through the through opening 40 is located in a sidewall section of the housing 2 of the injection device 1. As shown in FIG. 2 the through opening 40 and the second optical coupling 14 are located in a longitudinal mid-section of the housing 2. When attached to the injection device 1, the body 51 of the supplementary device 50 overlaps with the through opening 40 and hence with the second optical coupling 14. As indicated in FIG. 5, the first optical coupling 54 and the second optical coupling 14 substantially overlap so as to provide a sufficient coupling of light generated by the supplementary device 50 towards the second optical coupling 14.

In the embodiment as shown in FIG. 3 the optical coupling 14 is arranged in or near the edge of another through opening 16 configured as an inspection window in the sidewall of the elongated housing 2. In FIG. 4 there are provided two individual optical couplings 14 located on opposite sides of the inspection window. Generally, the location of the optical couplings 14 and of a respective through opening 16, 40 can be located at any arbitrary position accessible from outside the housing 2 of the injection device 1. With the implementation as shown in FIGS. 8-10 and 12 the second optical coupling 14 may be located in or at a proximal end face of the housing 2 of the injection device 1. It may be also located inside the housing 2 in such a way that it is in a direct line of slight with the first optical coupling 54.

As it is further apparent from the cross-sections according to FIGS. 5 and 6 the second optical coupling 14 is connected to a visual indicator 18. There is typically provided a light conductor 20 that connects the second optical coupling 14 with the visual indicator 18. The visual indicator 18 and the second optical coupling 14 may be located rather remote from each other. Here, the light conductor 20 provides a connection between the second optical coupling 14 and the visual indicator 18. In the embodiment as shown in FIGS. 5 and 6 the visual indicator 18 as well as the second optical coupling 14 are integrated into one and the same light conductor 20. As shown in FIG. 6 representing a distal portion of a cross-section extending at an angle of 90° relative to the cross-section according to FIG. 5 it is apparent that there may be provided several visual indicators 18 that are connected to one and the same second optical coupling 14.

Here, the upper visual indicator 18 as shown in FIG. 6 is connected via a light conductor 30 with the second optical coupling 14. The lower indicator 18 is provided by another light conductor 20 also connected to the second optical coupling 14. The two light conductors 20, 30 extend parallel and comprise a kind of a light bar. As shown in FIG. 2 and FIG. 5 the light conductors 20, 30 and the visual indicators 18 may extend along a side edge of the inspection window 16 so as to provide a particular illumination or an illuminating effect that is capable to assist a user in using the injection device 1 and/or in using the supplementary device 50. The visual indicators 18 may comprise a frosted or roughened surface 28 as indicated in FIG. 5. In this way a light beam transmitted and guided through the light conductors 20, 30 will spread in manifold and arbitrary directions as it leaves the light conductors 20, 30.

For transmitting the light coupled into the second optical coupling 14 the light conductors 20, 30 comprise various reflectors 19, 22, 23, 32 and 33 by way of which a light beam generated by the at least one light source 52 and coupled into the second optical coupling 14 is guided and transferred towards the visual indicator 18. For instance, a light beam entering the second optical coupling 14 as illustrated in FIG. 5 will reflect at the reflector 19 provided at an inside facing border of the light conductor 20. The reflector 19 is for instance oriented at a 45° orientation with regard to both, the elongation of the light conductor 20 as well as with regard to the orientation or position of the at least one light source 52.

Here, a light beam entering the second optical coupling 14 may experience a total reflection at the reflector 19 and may then propagate along the extension and elongation of the light conductor 20. In order to branch off into the two light conductors 20 and 30 each light conductor 20, 30 may be symmetrically arranged with regard to the reflector 19. For each of the light conductors 20, 30 there is provided a reflector 22, 32 by way of which the incoming light beam or portions thereof will be split and reflected outwardly as shown in FIG. 6. The light beams will be directed to another reflector 23, 33, respectively by way of which the incident light beams will then finally propagate along the light conductors 20, 30 that may comprises a straight and elongated shape.

There are different application scenarios conceivable. For instance with a multi-color LED the visual indicators 18 may be illuminated with a white color before an injection procedure takes place. With a removal of the cap 12, which may be sensed by the supplementary device 50 and the sensor arrangement 60, the visual indicators 18 may turn into a yellow color. When initiating a dose dispensing or injection procedure or when reaching the end of an injection the visual indicators 18 may start to blink or to flash thereby indicating that the end of an injection procedure has been reached and that the user should wait for a certain while before retracting the needle 5 from an injection site. When the injection device 1 is ready to be taken away from the injection site this may be indicated to a user via the visual indicators 18 showing up in a green color.

In the following a typical procedure and a typical use of the kit 90 is described. First of all the supplementary device 50 is attached to the injection device 1. Alternatively, the kit 90 that consists of the supplementary device 50 and the injection device 1 is already preassembled when delivered to a user or consumer. Then and as a first step 100 of a method of monitoring the operation of the injection device 1 the supplementary device 50 is activated. The activation of the supplementary device 50 may be conducted by some kind of an actuator, such as a button or some comparable touch-sensitive switch on, in or at the body 51 of the supplementary device 50.

Alternatively, the supplementary device 50 may be activated by means of a software 84 processed and executed by the external electronic device 80. Hence, the supplementary device 50 may be in a permanent standby operation in which it is and remains accessible via the wireless communication interface 58. In a subsequent step 102 a state of the injection device 1 is detected, typically by means of the sensor assembly 60 of the supplementary device 50. For instance, an actual position of the plunger 6 is determined, e.g. by means of the optical sensor 61. Alternatively or additionally, also the ambient temperature and/or a temperature of the medicament contained inside the cartridge 13 may be determined or measured. If the state of the injection device allows execution of an injection procedure then a user may perform such a dose dispensing procedure.

In step 104 the supplementary device 50 will detect the start of such an injection procedure. During or after the injection procedure there will be provided a visual and/or audible feedback. The visual feedback may be provided and generated by the supplementary device 50. For instance, the at least one light source 52 will generate a characteristic and visually perceptible signal that is typically transferred from the first optical coupling 54 to the second optical coupling 14. Then, the visual indicator 18 provided at the housing 2 of the injection device 1 will be illuminated at a certain color or will show a characteristic sequence of a repetitive flashing of a light.

In addition to such a visual feedback there may be also provided an audible feedback. The audible feedback may be provided directly by the injection device 1, e.g. by means of its click sound generator 11. Additionally or alternatively also the supplementary device 50 may be equipped with some kind of an acoustic signal generator that is configured to generate the audible feedback. Further alternatively, the external electronic device 80 generates an audible sound in response to receive respective signals via the wireless communication interface 58, 88.

In a subsequent step 108 the end of an injection procedure is detected. Detection of the end of injection may be based on an acoustic detection, e.g. when the injection device 1 is configured to generate an audible sound or audible click noise that may be recorded by a microphone 63 of the supplementary device 50 or by a microphone of the external electronic device 80. In response to the detection of the end of an injection procedure the method may return to step 106 and to provide a characteristic visual and/or audible feedback to the user that dose injection has been completed. Concurrently and/or subsequently, in step 110 the supplementary device 50 may store injection-related information, such as date and time of injection, the amount of medicament injected, a duration of injection and other injection-related information or data, such as the type of medicament, ambient temperature and so on.

When the supplementary device 50 is connected to the external electronic device 80 in a subsequent step 112 previously stored or actually generated data and/or information may be transferred to the external electronic device 80. Based on the obtained data or information the external electronic device 80 may provide information for the user in step 114. Here, the external electronic device 80 may display useful instructions, such as history logs, the next medication date or indications on treatment of a particular disease. When the medicament contained inside the injection device 1 has been used up or when the medicament should no longer be used the injection device 1 may be subject to disposal in step 116.

It is to be mentioned here, that various modifications of the steps 100-116 may be made to the method of monitoring the operation of the injection device 1 or of a method of providing feedback to a user. In particular, prior to start injection, during injection and when detecting the end of injection the supplementary device 50 in conjunction with the injection device 1 may provide characteristic and specific illuminating effects to assist and/or to instruct a user prior, during and after execution of a dose setting procedure and/or a dose dispensing procedure. In the same or in a similar way the user may also be assisted by the mutual interaction of the supplementary device 50 with the external electronic device 80. Also here, prior to an injection procedure, during execution of the dose setting procedure and/or an injection procedure and after termination of the dose setting procedure and/or the injection procedure the external electronic device 80 may provide visual and/or audible feedback and assistance to the user.

In the present context, a distal end or a distal direction refers to that end of the injection device that is oriented towards a portion of a body of a person or an animal that should be subject to injection. A proximal direction or a proximal end refers to the opposite end of the injection device, which is typically opposite to the dispensing end of the injection device.

The term "drug" or "medicament", as used herein, means a pharmaceutical formulation containing at least one pharmaceutically active compound. In one embodiment, the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound. In a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis. In a further embodiment the pharmaceutically active compound comprises at least one peptide for the treatment and/or prophylaxis of diabetes mellitus or complications associated with diabetes mellitus such as diabetic retinopathy. In a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the invention as defined in the appended claims. Further, it is to be noted, that any reference numerals used in the appended claims are not to be construed as limiting the scope of the disclosure.

LIST OF REFERENCE NUMBERS 1 injection device
2 housing 3 mechanical connector
4 piston
5 needle
6 plunger
7 shroud
8 insert
9 spring
10 spring
11 click sound generator
12 cap
13 cartridge
14 optical coupling
15 drive mechanism
16 through opening
18 visual indicator
19 reflector
20 light conductor
22 reflector
23 reflector
25 extension
28 frosted surface
30 light conductor
32 reflector
33 reflector
40 through opening
50 supplementary device
51 body
52 light source
53 mechanical connector
54 optical coupling
55 electric energy source
56 processor
57 storage
58 communication interface
59 optical connection
60 sensor arrangement
61 optical sensor
62 temperature sensor
63 microphone
64 antenna
65 indicator
66 indicator
68 portion
71 illuminant
72 illuminant
80 external electronic device
81 processor
82 display
84 software
88 communication interface
90 kit
150 supplementary device
151 body

The invention claimed is:

1. A kit comprising:
an injection device for dispensing of a dose of a medicament, the injection device comprising:
a housing to accommodate a cartridge filled with the medicament and sealed with a piston towards a proximal end of the cartridge,
a drive mechanism comprising a plunger to operably engage with the piston of the cartridge to expel the dose of the medicament via a distal end of the cartridge,
at least one visual indicator attached to or arranged inside the housing and being visible from outside the housing, and
at least a second optical coupling arranged in or on the housing and connected to the at least one visual indicator in a light transmissive way; and
a supplementary device comprising:
a body attachable to the housing of the injection device, the body having a first portion facing towards the housing when attached to the housing,
at least one light source attached to the body, and
at least a first optical coupling located in or at the first portion, the at least one first optical coupling being connected to the at least one light source in a light transmissive way and optically connectable to the at least one second optical coupling arranged in or on the housing,
wherein the supplementary device is attachable to the housing of the injection device such that the first optical coupling and the at least one second optical coupling form an optical connection for transmitting light generated by the at least one light source of the supplementary device to the at least one visual indicator of the injection device and wherein the at least one visual indicator is visible from outside when the supplementary device is attached to the housing.

2. The kit according to claim 1, wherein the supplementary device further comprises an electric energy source configured to be connected to the at least one light source.

3. The kit according to claim 1, wherein the supplementary device further comprises a processor connected to the at least one light source and configured to control activation of the at least one light source.

4. The kit according to claim 1, wherein the supplementary device further comprises a sensor arrangement having at least one of an optical sensor, a temperature sensor, or a microphone to detect or to measure at least one state parameter of the injection device.

5. The kit according to claim 1, wherein the supplementary device further comprises a wireless communication interface to communicate with an external electronic device.

6. The kit according to claim 1, wherein the supplementary device is configured to communicate with a separate external electronic device that includes a display and wherein the supplementary device is displayless.

7. The kit according to claim 1, wherein the supplementary device further comprises at least one mechanical connector to releasably engage with a correspondingly shaped mechanical connector of the housing.

8. The kit according to claim 1, wherein the supplementary device further comprises at least one visual indicator connected to a processor to visually indicate a momentary state of the injection device.

9. The kit according to claim 1, wherein the at least one light source comprises a multi-color illuminant or wherein the at least one light source comprises several illuminants of different colors.

10. The kit according to claim 1, wherein the injection device further comprises at least one light conductor arranged inside the housing and having a first end provided with the at least one second optical coupling and having a second end forming the at least one visual indicator.

11. The kit according to claim 10, wherein one of the at least one visual indicator and the second end of the at least one light conductor is located:
at an end section of the housing,
in a window section of the housing, or
in an aperture formed in the housing.

12. The kit according to claim 1, wherein the housing comprises at least one through opening and wherein at least one of the at least one second optical coupling or the at least one visual indicator is arranged inside or extends into the at least one through opening.

13. The kit according to claim 1, wherein the at least one visual indicator comprises a frosted surface or roughened surface.

14. The kit according to claim 1, wherein the at least one visual indicator is located remote from the at least one second optical coupling.

* * * * *